United States Patent
Spiry et al.

(10) Patent No.: US 9,890,183 B2
(45) Date of Patent: Feb. 13, 2018

(54) AMINOSILICONE SOLVENT RECOVERY METHODS AND SYSTEMS

(71) Applicant: GENERAL ELECTRIC COMPANY, Schenectady, NY (US)

(72) Inventors: Irina Pavlovna Spiry, Glenville, NY (US); Robert James Perry, Niskayuna, NY (US); Benjamin Rue Wood, Niskayuna, NY (US); Surinder Prabhjot Singh, Niskayuna, NY (US); Rachel Lizabeth Farnum, Rensselaer, NY (US); Sarah Elizabeth Genovese, Delmar, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 14/962,199

(22) Filed: Dec. 8, 2015

(65) Prior Publication Data
US 2017/0158717 A1    Jun. 8, 2017

(51) Int. Cl.
| | | |
|---|---|---|
| *C07F 7/00* | (2006.01) | |
| *C07F 7/20* | (2006.01) | |
| *B01D 53/00* | (2006.01) | |
| *B01D 53/14* | (2006.01) | |
| *B01D 53/18* | (2006.01) | |
| *B01D 5/00* | (2006.01) | |

(52) U.S. Cl.
CPC ............ *C07F 7/20* (2013.01); *B01D 5/009* (2013.01); *B01D 53/002* (2013.01); *B01D 53/1425* (2013.01); *B01D 53/1475* (2013.01); *B01D 53/18* (2013.01); *B01D 2252/204* (2013.01)

(58) Field of Classification Search
CPC ........ C07F 7/20; B01D 53/1475; B01D 53/18
USPC ....................................................... 556/425
See application file for complete search history.

(56) References Cited

U.S. PATENT DOCUMENTS

| | | |
|---|---|---|
| 8,647,413 B2 | 2/2014 | Soloveichik et al. |
| 8,709,367 B2 | 4/2014 | Pinard Westendorf et al. |
| 8,795,415 B2 | 8/2014 | Katz et al. |
| 2009/0151564 A1 | 6/2009 | Handagama et al. |
| 2010/0029466 A1 | 2/2010 | Woodhouse |
| 2012/0207659 A1* | 8/2012 | Pinard Westendorf ........ B01D 53/1425 423/228 |
| 2013/0202517 A1 | 8/2013 | Ayala et al. |
| 2013/0323148 A1 | 12/2013 | Vipperla |

FOREIGN PATENT DOCUMENTS

| | | |
|---|---|---|
| WO | 2013028391 A1 | 2/2013 |
| WO | 2014127410 A1 | 8/2014 |

OTHER PUBLICATIONS

Perry et al., ChemSusChem 2010, 3, 919-930.*
Perry et al., ChemSusChem 2010, 3(8), 919-930.*
Perry et al., "Aminosilicone Solvents for CO2 Capture", ChemSusChem energy & materials, vol. 3, Issue 8, pp. 919-930, Aug. 23, 2010.

* cited by examiner

*Primary Examiner* — Sudhakar Katakam
*Assistant Examiner* — Kofi Adzamli
(74) *Attorney, Agent, or Firm* — Pabitra K. Chakrabarti

(57) ABSTRACT

The present invention is directed to aminosilicone solvent recovery methods and systems. The methods and systems disclosed herein may be used to recover aminosilicone solvent from a carbon dioxide containing vapor stream, for example, a vapor stream that leaves an aminosilicone solvent desorber apparatus. The methods and systems of the invention utilize a first condensation process at a temperature from about 80° C. to about 150° C. and a second condensation process at a temperature from about 5° C. to about 75° C. The first condensation process yields recovered aminosilicone solvent. The second condensation process yields water.

10 Claims, 1 Drawing Sheet

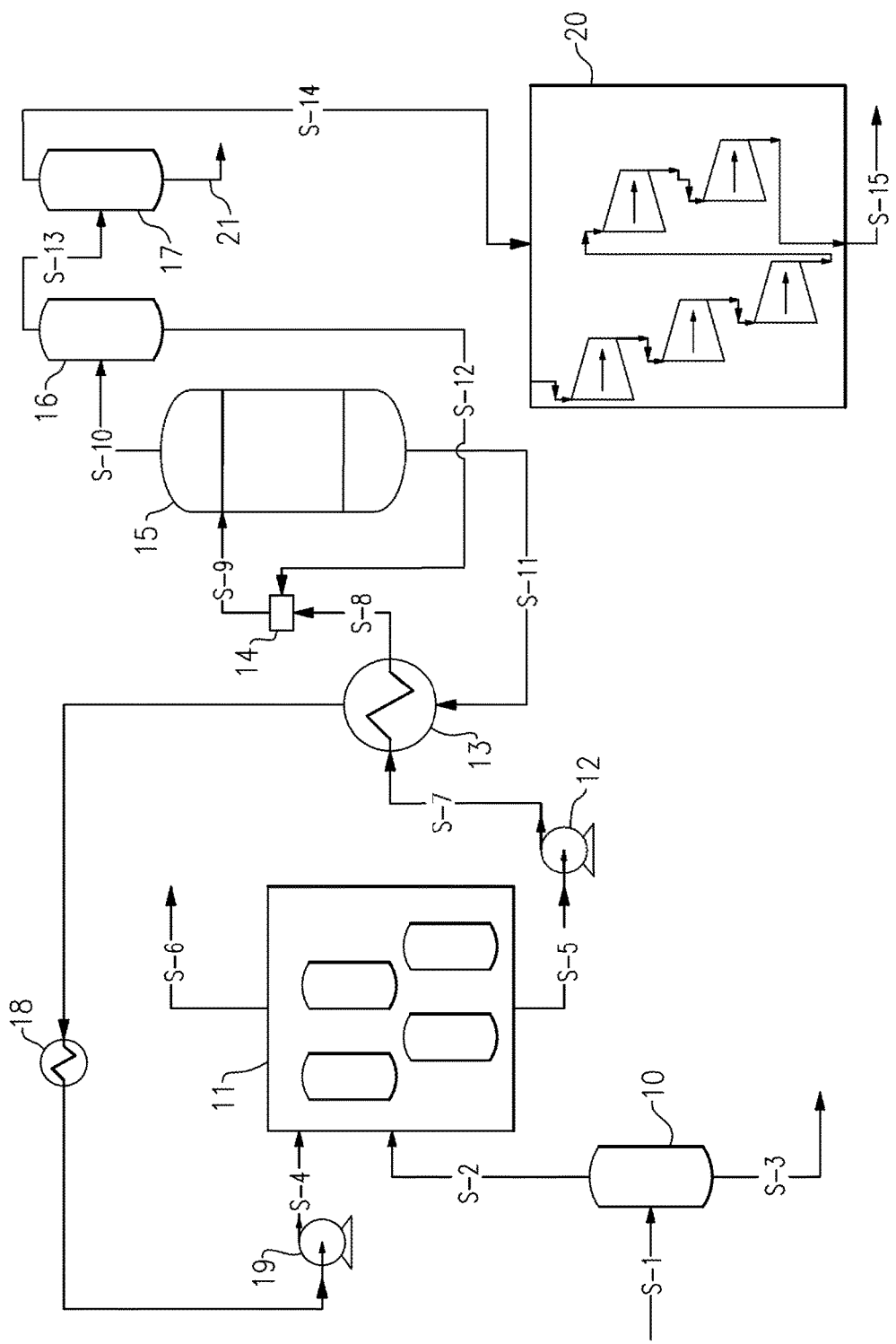

AMINOSILICONE SOLVENT RECOVERY METHODS AND SYSTEMS

STATEMENT ON FEDERALLY SPONSORED RESEARCH OR DEVELOPMENT

This invention was made with government support under grant number DEFE0013755 awarded by the U.S. Department of Energy National Energy Technology Laboratory. The government has certain rights in the invention.

FIELD OF THE INVENTION

This invention relates to methods and systems for recovering aminosilicone solvent from a vapor stream, for example, a vapor stream that leaves an aminosilicone solvent desorber apparatus.

BACKGROUND OF THE INVENTION

The emission of carbon dioxide gas into the atmosphere from industrial sources such as power plants is now considered to be a principal cause of the "greenhouse effect", which contributes to global climate change. In response, efforts are underway to reduce carbon dioxide emissions. Many different processes have been developed to accomplish this task. Examples include polymer and inorganic membrane permeation; removal of carbon dioxide by adsorbents such as molecular sieves; cryogenic separation; and scrubbing with a solvent that is chemically reactive with carbon dioxide, or which has a physical affinity for the gas.

Most carbon capture techniques, such as those used in acid gas removal systems or low-pressure carbon dioxide absorbers in gasification units, use dilute aqueous solutions operated at low temperatures, of about 40° F. or below, to remove carbon dioxide from flue gas streams, e.g. exhaust gas produced at power plants, to produce a stream of high purity carbon dioxide. The high purity carbon dioxide product is then used in enhanced oil recovery (EOR), gasification applications, or sequestered in saline aquifers.

Recently, a new process for carbon dioxide recovery using an aminosilicone solvent has been developed, as disclosed in International Application Publication No. WO 2013/028391, U.S. Patent Application Publication No. 2013/0202517, and in Perry et al., Aminosilicone Solvents for $CO_2$ Capture, ChemSusChem Energy & Materials, 3(8): 919-930 (2010) ("Perry et al."). Typical carbon dioxide recovery using an aminosilicone solvent involves contacting an exhaust gas stream containing carbon dioxide (such as a gas turbine exhaust) with a lean aminosilicone solvent that is fed to an absorption apparatus. The lean aminosilicone solvent reacts with carbon dioxide and forms rich aminosilicone solvent. Desorption of the carbon dioxide from aminosilicone solvent occurs in a desorber apparatus, which is a high pressure Continuous Stirred Tank Reactor (CSTR). The desorption process generates a carbon dioxide-rich vapor stream, which leaves the desorber apparatus. However, this vapor stream also contains significant amounts of valuable aminosilicone solvent, such as 1,5-bis-(3-aminopropyl)hexamethyl-trisiloxane (GAP-1) and GAP-1 carbamate. Because loss of the aminosilicone solvent with the vapor stream is wasteful, recovery of the aminosilicone solvent from the vapor stream is desired.

SUMMARY OF THE INVENTION

The present invention relates to aminosilicone solvent recovery methods and systems. The methods and systems disclosed herein may be used to recover aminosilicone solvent from a vapor stream, for example, a vapor stream that leaves an aminosilicone solvent desorber apparatus.

The methods and systems of the invention utilize a first condensation process at a temperature from about 80° C. to about 150° C. and a second condensation process at a temperature from about 5° C. to about 75° C. The first condensation process yields recovered aminosilicone solvent. The second condensation process yields water.

Thus, in one embodiment, the invention is directed to a method for recovering aminosilicone solvent from a first gas stream, wherein the first gas stream comprises lean aminosilicone solvent, carbon dioxide, and water vapor, the method comprising:
  performing a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  performing a second condensation process, wherein the second condensation process comprises condensing the second gas stream at a temperature from about 5° C. to about 75° C. to form a waste water stream and a third gas stream; wherein the waste water stream comprises water and the third gas stream comprises carbon dioxide.

In another embodiment, the invention is directed to a method for capturing carbon dioxide from a flue gas, the method comprising:
  performing an absorption process, wherein the absorption process comprises contacting the flue gas with a lean stream to form a clean flue gas stream and a rich stream, wherein the lean stream comprises lean aminosilicone solvent, and wherein the rich stream comprises rich aminosilicone solvent;
  performing a desorption process, wherein the desorption process comprises heat treating the rich stream at a temperature from about 120° C. to about 160° C. to form the lean stream and a first gas stream, wherein the first gas stream comprises lean aminosilicone solvent, carbon dioxide, and water vapor;
  performing a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  performing a second condensation process, wherein the second condensation process comprises condensing the second gas stream at a temperature from about 5° C. to about 75° C. to form a waste water stream and a third gas stream; wherein the waste water stream comprises water and the third gas stream comprises carbon dioxide.

In another embodiment, the invention is directed to a system for recovering aminosilicone solvent from a first gas stream, wherein the first gas stream comprises lean aminosilicone solvent, carbon dioxide, and water vapor, the system comprising:
  a first condenser apparatus operable to receive the first gas stream and to perform a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and a second condenser apparatus operable to receive the second gas stream and to perform a second condensation process, wherein the second condensation process comprises condensing the second gas stream at a temperature from about 5° C. to about 75° C. to form a waste water stream and a third gas stream, wherein the waste water stream comprises water and the third gas stream comprises carbon dioxide.

In yet another embodiment, the invention is directed to a system for capturing carbon dioxide from a flue gas, the system comprising:

an absorption apparatus operable to receive the flue gas and a lean stream and to perform an absorption process, wherein the absorption process comprises contacting the flue gas with the lean stream to form a clean flue gas stream and a rich stream, wherein the lean stream comprises lean aminosilicone solvent, and wherein the rich stream comprises rich aminosilicone solvent;

a desorber apparatus operable to receive the rich stream and to perform a desorption process, wherein the desorption process comprises heat treating the rich stream at a temperature from about 120° C. to about 160° C. to form the lean stream and a first gas stream, wherein the first gas stream comprises lean aminosilicone solvent, carbon dioxide, and water vapor;

a first condenser apparatus operable to receive the first gas stream and to perform a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and a second condenser apparatus operable to receive the second gas stream and to perform a second condensation process, wherein the second condensation process comprises condensing the second gas stream at a temperature from about 5° C. to about 75° C. to form a waste water stream and a third gas stream, wherein the waste water stream comprises water and the third gas stream comprises carbon dioxide.

The methods and systems of the invention are advantageous because they recover all or almost all of aminosilicone solvent which is otherwise wasted as it leaves the desorber apparatus in the carbon dioxide-rich vapor stream.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 1 is a schematic diagram of one embodiment of an aminosilicone solvent recovery system of the invention.

DETAILED DESCRIPTION OF THE INVENTION

In the following specification and the claims which follow, reference will be made to a number of terms, which shall be defined to have the following meanings.

The singular forms "a", "an", and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aminosilicone solvent" refers to a composition of one or more types of silicone-based compounds having nitrogen containing group or groups, wherein these compounds have an ability to reversibly react with carbon dioxide or have an affinity for carbon dioxide. The aminosilicone solvent compounds are known in the art and are described, for example, in Perry et al., International Patent Application Publication No. WO 2013/028391, and U.S. Patent Application Publication No. 2013/0202517. The aminosilicone solvent may also include additional ingredients, such as cosolvents, e.g. triethylene glycol.

As used herein, the term "GAP-1" or "GAP1" refers to an aminosilicone compound with an average structural composition of 1,5-bis-(3-aminopropyl)hexamethyl-trisiloxane, described in International Patent Application Publication No. WO 2013/028391, page 11. GAP-1 is an example of lean aminosilicone solvent.

As used herein, the term "GAP-1 carbamate" or "GAP1CARB" refers to GAP-1 compound that has reacted with carbon dioxide. GAP-1 carbamate is an example of rich aminosilicone solvent.

As used herein, the term "lean aminosilicone solvent" refers to an aminosilicone solvent that is unreacted with carbon dioxide or not complexed with carbon dioxide. A lean stream includes lean aminosilicone solvent but may also include small amounts of rich aminosilicone solvent.

As used herein, the term "rich aminosilicone solvent" refers to an aminosilicone solvent that has reacted with carbon dioxide or complexed with carbon dioxide. A rich stream includes rich aminosilicone solvent but may also include small amounts of lean aminosilicone solvent.

As used herein, the term "flue gas" refers to a combustion exhaust gas, which includes carbon dioxide and may include other components, such as nitrogen and water vapor.

As used herein, the term "clean flue gas" refers to a combustion exhaust gas that has been subjected to the described herein absorption process. Accordingly, the clean flue gas has lower carbon dioxide content than a flue gas that has not been subjected to the described herein absorption process.

As used herein, the term "absorption process" refers to a known in the art process in which a gas containing carbon dioxide is contacted with lean aminosilicone solvent, which results in formation of a rich aminosilicone solvent. Thus, the absorption process includes contacting the flue gas with a lean stream to form a clean flue gas stream and a rich stream, wherein the lean stream includes lean aminosilicone solvent, and wherein the rich stream includes rich aminosilicone solvent.

As used herein, the term "absorption apparatus" refers to a known in the art apparatus operable to perform the absorption process.

As used herein, the term "desorption process" refers to a known in the art process in which rich aminosilicone solvent is treated to form lean aminosilicone solvent and carbon dioxide. Thus, the desorption process includes heat treating the rich stream at a temperature from about 120° C. to about 160° C. to form the lean stream and a first gas stream, wherein the first gas stream comprises lean aminosilicone solvent, carbon dioxide, and water vapor.

As used herein, the term "desorber apparatus" refers to a known in the art apparatus operable to perform the desorption process.

As used herein, the term "condensation process" refers to a known in the art process in which a physical state of matter is changed from a gas phase to a liquid phase. In the methods of the invention, condensation processes result in liquid phase products and gas phase products.

As used herein, the term "condenser apparatus" refers to a known in the art apparatus operable to perform the condensation process.

As used herein, the term "compression process" refers to a known in the art process wherein gas pressure is increased and gas volume is reduced, thereby forming a compressed composition. An example of a compressed composition is a composition that includes high pressure carbon dioxide.

As used herein, the term "compressor apparatus" refers to a known in the art apparatus operable to perform the compression process.

As used herein, the term "high pressure carbon dioxide" refers to carbon dioxide at a pressure greater than atmospheric.

When the described herein methods refer to a specified method step performed on a specified stream, this specified method step is generally to be performed in an apparatus operable to perform the specified method step.

In one embodiment, the invention is directed to a method for recovering aminosilicone solvent from a first gas stream, wherein the first gas stream comprises lean aminosilicone solvent, carbon dioxide, and water vapor, the method comprising:
  performing a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  performing a second condensation process, wherein the second condensation process comprises condensing the second gas stream at a temperature from about 5° C. to about 75° C. to form a waste water stream and a third gas stream; wherein the waste water stream comprises water and the third gas stream comprises carbon dioxide.

The first gas stream and the recovered aminosilicone stream may further comprise triethylene glycol (TEG). The first gas stream may further include rich aminosilicone solvent. The recovered aminosilicone stream may also further include rich aminosilicone solvent. Furthermore, the recovered aminosilicone stream may also include water, such as water vapor, TEG, or mixtures thereof. The second gas stream may further include lean aminosilicone solvent, rich aminosilicone solvent, TEG, or mixtures thereof. The waste water stream may further include lean aminosilicone solvent, rich aminosilicone solvent, TEG, or mixtures thereof. The third gas stream may further include water, such as water vapor, lean aminosilicone solvent, rich aminosilicone solvent, TEG, or mixtures thereof.

In another embodiment, the method further includes, prior to performing the first condensation process, performing a desorption process, wherein the desorption process comprises heat treating a rich stream at a temperature from about 120° C. to about 160° C. to form a lean stream and the first gas stream, wherein the rich stream comprises rich aminosilicone solvent, and wherein the lean stream comprises lean aminosilicone solvent.

In an additional embodiment, the first condensation process comprises condensing the first gas stream at a temperature from about 80° C. to about 110° C. In another embodiment, the first condensation process comprises condensing the first gas stream at a temperature from about 85° C. to about 95° C. In yet another embodiment, the first condensation process comprises condensing the first gas stream at a temperature of about 90° C.

In an additional embodiment, the second condensation process comprises condensing the second gas stream at a temperature from about 20° C. to about 70° C. In another embodiment, the second condensation process comprises condensing the second gas stream at a temperature from about 35° C. to about 45° C. In yet another embodiment, the second condensation process comprises condensing the second gas stream at a temperature of about 40° C.

In one embodiment, the method further includes performing a compression process on the third gas stream, wherein the compression process comprises compressing the third gas stream to form a compressed composition, wherein the compressed composition comprises high pressure carbon dioxide.

In another embodiment, the method further includes, prior to performing the desorption process, performing an absorption process, wherein the absorption process comprises contacting a flue gas with the lean stream to form a clean flue gas stream and the rich stream.

The present invention is also directed to a method for capturing carbon dioxide from a flue gas, the method comprising:
  performing an absorption process, wherein the absorption process comprises contacting the flue gas with a lean stream to form a clean flue gas stream and a rich stream, wherein the lean stream comprises lean aminosilicone solvent, and wherein the rich stream comprises rich aminosilicone solvent;
  performing a desorption process, wherein the desorption process comprises heat treating the rich stream at a temperature from about 120° C. to about 160° C. to form the lean stream and a first gas stream, wherein the first gas stream comprises lean aminosilicone solvent, carbon dioxide, and water vapor;
  performing a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  performing a second condensation process, wherein the second condensation process comprises condensing the second gas stream at a temperature from about 5° C. to about 75° C. to form a waste water stream and a third gas stream; wherein the waste water stream comprises water and the third gas stream comprises carbon dioxide.

In one embodiment, the first gas stream and the recovered aminosilicone stream may further comprise triethylene glycol.

In another embodiment, the desorption process further comprises heat treating the recovered aminosilicone stream at a temperature from about 120° C. to about 160° C. to form the lean stream and, optionally, the first gas stream.

In an additional embodiment, the first condensation process comprises condensing the first gas stream at a temperature from about 80° C. to about 110° C. In another embodiment, the first condensation process comprises condensing the first gas stream at a temperature from about 85° C. to about 95° C. In yet another embodiment, the first condensation process comprises condensing the first gas stream at a temperature of about 90° C.

In an additional embodiment, the second condensation process comprises condensing the second gas stream at a temperature from about 20° C. to about 70° C. In another embodiment, the second condensation process comprises condensing the second gas stream at a temperature from about 35° C. to about 45° C. In yet another embodiment, the second condensation process comprises condensing the second gas stream at a temperature of about 40° C.

In one embodiment, the method further includes performing a compression process on the third gas stream, wherein the compression process comprises compressing the third gas stream to form a compressed composition, wherein the compressed composition comprises high pressure carbon dioxide.

The present invention is also directed to a system for recovering aminosilicone solvent from a first gas stream, wherein the first gas stream comprises lean aminosilicone solvent, carbon dioxide, and water vapor, the system comprising:
  a first condenser apparatus operable to receive the first gas stream and to perform a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  a second condenser apparatus operable to receive the second gas stream and to perform a second condensation process, wherein the second condensation process comprises condensing the second gas stream at a temperature from about 5° C. to about 75° C. to form a waste water stream and a third gas stream, wherein the waste water stream comprises water and the third gas stream comprises carbon dioxide.

In one embodiment, the first gas stream and the recovered aminosilicone stream may further comprise triethylene glycol.

In another embodiment, the system further includes a desorber apparatus operable to receive a rich stream and to perform a desorption process, wherein the desorption process comprises heat treating a rich stream at a temperature from about 120° C. to about 160° C. to form a lean stream and the first gas stream, wherein the rich stream comprises rich aminosilicone solvent, and wherein the lean stream comprises lean aminosilicone solvent.

In yet another embodiment, the desorber apparatus may be also operable to receive the recovered aminosilicone stream, wherein the desorption process further comprises heat treating the recovered aminosilicone stream at a temperature from about 120° C. to about 160° C. to form the lean stream and, optionally, the first gas stream.

In an additional embodiment, the first condensation process comprises condensing the first gas stream at a temperature from about 80° C. to about 110° C. In another embodiment, the first condensation process comprises condensing the first gas stream at a temperature from about 85° C. to about 95° C. In yet another embodiment, the first condensation process comprises condensing the first gas stream at a temperature of about 90° C.

In an additional embodiment, the second condensation process comprises condensing the second gas stream at a temperature from about 20° C. to about 70° C. In another embodiment, the second condensation process comprises condensing the second gas stream at a temperature from about 35° C. to about 45° C. In yet another embodiment, the second condensation process comprises condensing the second gas stream at a temperature of about 40° C.

In another embodiment, the system further includes a compressor apparatus operable to receive the third gas stream and to perform a compression process on the third gas stream, wherein the compression process comprises compressing the third gas stream to form a compressed composition, wherein the compressed composition comprises high pressure carbon dioxide.

In another embodiment, the system further includes an absorption apparatus operable to receive a flue gas and the lean stream and to perform an absorption process, wherein the absorption process comprises contacting the flue gas with the lean stream to form a clean flue gas stream and the rich stream.

The present invention is also directed to a system for capturing carbon dioxide from a flue gas, the system comprising:
  an absorption apparatus operable to receive the flue gas and a lean stream and to perform an absorption process, wherein the absorption process comprises contacting the flue gas with the lean stream to form a clean flue gas stream and a rich stream, wherein the lean stream comprises lean aminosilicone solvent, and wherein the rich stream comprises rich aminosilicone solvent;
  a desorber apparatus operable to receive the rich stream and to perform a desorption process, wherein the desorption process comprises heat treating the rich stream at a temperature from about 120° C. to about 160° C. to form the lean stream and a first gas stream, wherein the first gas stream comprises lean aminosilicone solvent, carbon dioxide, and water vapor;
  a first condenser apparatus operable to receive the first gas stream and to perform a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
  a second condenser apparatus operable to receive the second gas stream and to perform a second condensation process, wherein the second condensation process comprises condensing the second gas stream at a temperature from about 5° C. to about 75° C. to form a waste water stream and a third gas stream, wherein the waste water stream comprises water and the third gas stream comprises carbon dioxide.

In one embodiment, the first gas stream and the recovered aminosilicone stream may further comprise triethylene glycol.

In one embodiment, the desorber apparatus is operable to receive the recovered aminosilicone stream, wherein the desorption process further comprises heat treating the recovered aminosilicone stream at a temperature from about 120° C. to about 160° C. to form the lean stream and, optionally, the first gas stream.

In an additional embodiment, the first condensation process comprises condensing the first gas stream at a temperature from about 80° C. to about 110° C. In another embodiment, the first condensation process comprises condensing the first gas stream at a temperature from about 85° C. to about 95° C. In yet another embodiment, the first condensation process comprises condensing the first gas stream at a temperature of about 90° C.

In an additional embodiment, the second condensation process comprises condensing the second gas stream at a temperature from about 20° C. to about 70° C. In another embodiment, the second condensation process comprises condensing the second gas stream at a temperature from about 35° C. to about 45° C. In yet another embodiment, the second condensation process comprises condensing the second gas stream at a temperature of about 40° C.

In one embodiment, the system further includes a compressor apparatus operable to receive the third gas stream and to perform a compression process on the third gas stream, wherein the compression process comprises compressing the third gas stream to form a compressed composition, wherein the compressed composition comprises high pressure carbon dioxide.

A computer simulation of our method was performed using ASPEN PLUS® software. The computer simulation was based on one embodiment of the aminosilicone recovery method, which is shown in a schematic diagram of FIG. 1. With reference to FIG. 1, this embodiment of aminosilicone recovery method involves directing flue gas in a conduit S-1 into direct contact cooler (DCC) 10 to partially remove water in a conduit S-3 from the flue gas. The flue gas is then taken by conduit S-2 into an absorption apparatus 11 wherein lean aminosilicone solvent is contacted with the flue gas in an absorption process.

The absorption process forms a clean flue gas, which leaves the absorption apparatus 11 by conduit S-6. The absorption process also forms a rich stream, which includes rich aminosilicone solvent. The rich stream moves in FIG. 1 via conduits S-5, S-7, S-8, and S-9. The rich stream in conduit S-5 passes through rich solvent pump 12, passes through conduit S-7, passes through rich lean heat exchanger 13 and enters conduit S-8. The rich stream in conduit S-8 then passes through a T in the line 14, is mixed with recovered aminosilicone from conduit S-12, and enters conduit S-9, which leads the rich stream into a desorber apparatus 15.

The desorber apparatus performs a desorption process and forms a lean stream which enters conduit S-11, wherein the lean stream includes lean aminosilicone solvent. The lean stream is recycled back to the absorption apparatus 11 by passing through the rich lean heat exchanger 13, lean cooler 18, and lean solvent pump 19. The lean stream exits the lean solvent pump 19 via conduit S-4 and enters the absorption apparatus 11. The desorption process also forms a first gas stream which enters conduit S-10. The first gas stream includes lean aminosilicone solvent, carbon dioxide, and water vapor.

From the conduit S-10, the first gas stream enters a first condenser apparatus 16 wherein a first condensation process is performed. The computer modeling predicts that the temperature of the first condensation process should be from about 80° C. to about 150° C., with an optimal temperature at about 90° C. The first condensation process forms a recovered aminosilicone stream which enters conduit S-12. The recovered aminosilicone stream includes lean aminosilicone solvent. The recovered aminosilicone stream could be directed to the desorber apparatus 15 via conduits S-12 and then S-9, mixing with the rich aminosilicone from conduit S-8 in the T 14 before entering conduit S-9. The first condensation process also forms a second gas stream which enters conduit S-13. The second gas stream includes carbon dioxide and water vapor.

The second gas stream is directed by conduit S-13 into a second condenser apparatus 17 wherein a second condensation process is performed. The computer modeling predicts that the temperature of the second condensation process should be from about 5° C. to about 75° C., with an optimal temperature at about 40° C. The second condensation process forms a waste water stream, which enters conduit 21. The waste water stream includes water. The second condensation process also forms a third gas stream which enters conduit S-14. The third gas stream includes carbon dioxide.

The third gas stream could be sent via conduit S-14 to a compressor apparatus 20, wherein a compression process is performed. The compression process forms a compressed composition, which can exit the compressor apparatus via conduit S-15. The compressed composition includes high pressure carbon dioxide.

The following Table 1 shows computer model predicted compositions in conduits S-10, S-13, S-13, S-14, and in waste water conduit 21 when the temperature of the first condensation process is 90° C. and the temperature of the second condensation process is 40° C.

TABLE 1

|  | S-10 | S-13 | S-12 Recycle | S-14 | Waste Water |
|---|---|---|---|---|---|
| Mass Flow lb/hr | | | | | |
| $H_2O$ | 91419.2 | 78979.61 | 12439.59 | 8095.387 | 70884.23 |
| $CO_2$ | 1.14E+06 | 1137350 | 69.36471 | 1.14E+06 | 323.3066 |
| $N_2$ | 3862.315 | 3862.286 | 0.0290088 | 3862.261 | 0.0252133 |
| $O_2$ | 2.1169 | 2.116897 | 3.40E−06 | 2.116872 | 2.54E−05 |
| GAP1 | 18273.29 | 1108.685 | 17164.59 | 1.105878 | 1107.579 |
| GAP1CARB | 7370.762 | 453.2457 | 6917.52 | 0.4772997 | 452.7684 |
| TEG | 1420.259 | 2.659491 | 1417.599 | 8.19E−06 | 2.659483 |
| Mass Frac | | | | | |
| $H_2O$ | 7.26% | 6.46% | 32.73% | 0.70% | 97.41% |
| $CO_2$ | 90.29% | 93.09% | 0.18% | 98.96% | 0.44% |
| $N_2$ | 0.31% | 0.32% | 0.00% | 0.34% | 0.00% |
| $O_2$ | 0.00% | 0.00% | 0.00% | 0.00% | 0.00% |
| GAP1 | 1.45% | 0.09% | 45.16% | 0.00% | 1.52% |

TABLE 1-continued

|  | S-10 | S-13 | S-12 Recycle | S-14 | Waste Water |
|---|---|---|---|---|---|
| GAP1CARB | 0.59% | 0.04% | 18.20% | 0.00% | 0.62% |
| TEG | 0.11% | 0.00% | 3.73% | 0.00% | 0.00% |
| Total Flow lb/hr | 1,259,770 | 1,221,760 | 38,009 | 1,148,990 | 72,771 |
| Total Flow cuft/hr | 3.75E+06 | 3381550 | 873.4362 | 2.54E+06 | 1203.225 |
| Temperature F. | 248 | 194 | 194 | 104 | 104 |
| Pressure psia | 63 | 63 | 63 | 63 | 63 |
| Vapor Frac | 0.9992151 | 1 | 0 | 1 | 0 |
| Liquid Frac | 7.85E−04 | 0 | 1 | 0 | 1 |

As can be seen in Table 1, the recovered aminosilicone stream in conduit S-12 is predicted to recover almost all of aminosilicone solvent (i.e., "GAP1" and "GAP1CARB") which leaves the desorber apparatus 15 in the first gas stream in conduit S-10. Furthermore, the waste water stream in conduit 21 is predicted to contain only very small amounts of aminosilicone solvent. In other embodiments of the methods and systems of the invention, the waste water stream may contain no detectable amount of aminosilicone solvent, which would allow for the waste water stream to be sent for waste water treatment.

This written description uses examples to disclose embodiments of the invention, including the best mode, and also to enable any person skilled in the art to practice the invention, including making and using any devices or systems and performing any incorporated methods. The patentable scope of the invention is not limited to the scope of the provided examples, and may include other examples that occur to those skilled in the art. Such other examples are intended to be within the scope of the claims if they have structural elements or method steps that do not differ from the literal language of the claims, or if they include equivalent structural elements or method steps with insubstantial differences from the literal language of the claims.

EXAMPLES

Example 1

An experiment was performed to confirm the above described computer simulation. In a lab-scale apparatus for a two stage condensation process, a mixture of GAP-1 and water (150 mL of GAP-1 and 300 mL of deionized water) was heated to 130° C. in a glass flask and exposed to a rapid flow of nitrogen introduced through a gas dispersion tube to volatilize the mixture of GAP-1 and water. This was to simulate a vapor containing both GAP-1 and water. The pressure throughout the system was 1 atmosphere. The contents of the flask were foaming vigorously.

The vapor that was produced was directed to a first stage condenser held at 130° C. and a small amount of liquid was collected in a first receiving glass flask held at 135° C. The bulk of the vapor continued to a second condenser held at approximately 15° C. A second receiving glass flask connected to the second condenser captured the condensed liquid. The experiment was performed for 30 minutes. At the end of 30 minutes, the volume of material collected in the first receiving flask was about 2-3 mL and the volume of material collected in the second receiving flask was 120 mL.

Proton NMR analysis of the two liquid samples collected from each receiving flask showed that the first receiving flask collected approximately 10 times more GAP-1 than the second receiving flask. Specifically, the first receiving flask contained 2.9 wt/wt % GAP-1 and 97.1 wt/wt % water, while the second receiving flask contained 0.3% GAP-1 and 99.7% water. This demonstrates that preferential condensation of the GAP material occurs in the first stage of this process with nearly pure water collected in the second receiving flask. The absolute quantities of the GAP collected were small due to a non-optimized design of this lab-scale apparatus, which was not efficient at volatilizing the GAP component of the mixture.

Example 2

An additional experiment was also performed to confirm the above described computer simulation. In a lab-scale apparatus for a two stage condensation process, a mixture of GAP-1 and water (100 mL of GAP-1 and 500 mL of deionized water) was heated to 155-160° C. in a 1 L round bottom glass flask and exposed to a rapid flow of nitrogen introduced through a gas dispersion tube to volatilize the mixture of GAP-1 and water. This was to simulate a vapor containing both GAP-1 and water. The pressure throughout the system was 1 atmosphere. The contents of the flask were foaming vigorously.

The vapor that was produced was directed to a first stage condenser held at 90° C. and a small amount of liquid was collected in a first receiving glass flask held at 135° C. The bulk of the vapor continued to a second condenser held at 40° C. A second receiving glass flask connected to the second condenser captured the condensed liquid. The experiment was performed for 30 minutes. At the end of 30 minutes, the volume of material collected in the first receiving flask was 35 mL and the volume of material collected in the second receiving flask was 150 mL.

Proton NMR analysis of the two liquid samples collected from each receiving flask showed that the first receiving flask collected approximately 7 times more GAP-1 than the first receiving flask. Specifically, the first receiving flask contained 2.2 wt/wt % GAP-1 and 97.8 wt/wt % water, while the second receiving flask contained 0.3% GAP-1 and 99.7% water. This further demonstrates that preferential condensation of the GAP material occurs in the first stage of this process with nearly pure water collected in the second receiving flask. The absolute quantities of the GAP collected were small due to a non-optimized design of this lab-scale apparatus, which was not efficient at volatilizing the GAP component of the mixture.

While only certain features of the invention have been illustrated and described herein, many modifications and changes will occur to those skilled in the art. It is, therefore, to be understood that the appended claims are intended to cover all such modifications and changes as falling within the true spirit of the invention.

Throughout this application, various references are referred to. The disclosures of these publications in their entireties are hereby incorporated by reference as if written herein.

What is claimed is:

1. A method for recovering aminosilicone solvent from a first gas stream, the method comprising:
    performing an absorption process, wherein the absorption process comprises contacting a flue gas with a lean stream to form a clean flue gas stream and a rich stream;
    performing a desorption process, wherein the desorption process comprises heat treating the rich stream at a temperature from about 120° C. to about 160° C. to form a lean stream and the first gas stream, wherein the rich stream comprises rich aminosilicone solvent, and wherein the lean stream comprises lean aminosilicone solvent;
    performing a first condensation process, wherein the first condensation process comprises condensing the first gas stream at a temperature from about 80° C. to about 150° C. to form a recovered aminosilicone stream and a second gas stream, wherein the recovered aminosilicone stream comprises lean aminosilicone solvent and the second gas stream comprises carbon dioxide and water vapor; and
    performing a second condensation process, wherein the second condensation process comprises condensing the second gas stream at a temperature from about 5° C. to about 75° C. to form a waste water stream and a third gas stream; wherein the waste water stream comprises water and the third gas stream comprises carbon dioxide.

2. The method of claim 1, wherein the first gas stream and the recovered aminosilicone stream further comprise triethylene glycol.

3. The method of claim 1, wherein the first gas stream further comprises rich aminosilicone solvent.

4. The method of claim 1, wherein the recovered aminosilicone stream further comprises rich aminosilicone solvent.

5. The method of claim 1, wherein the desorption process further comprises heat treating the recovered aminosilicone stream at a temperature from about 120° C. to about 160° C. to form the lean stream and, optionally, the first gas stream.

6. The method of claim 1, further comprising:
    performing a compression process on the third gas stream, wherein the compression process comprises compressing the third gas stream to form a compressed composition, wherein the compressed composition comprises high pressure carbon dioxide.

7. The method of claim 1, wherein the first condensation process comprises condensing the first gas stream at a temperature from about 80° C. to about 110° C.

8. The method of claim 1, wherein the first condensation process comprises condensing the first gas stream at a temperature from about 85° C. to about 95° C.

9. The method of claim 1, wherein the second condensation process comprises condensing the second gas stream at a temperature from about 20° C. to about 70° C.

10. The method of claim 1, wherein the second condensation process comprises condensing the second gas stream at a temperature from about 35° C. to about 45° C.

* * * * *